United States Patent [19]
Desjarlais

[11] 3,976,491
[45] Aug. 24, 1976

[54] DIAZO COMPOSITIONS AND DIAZOTYPE MATERIALS PREPARED FROM SAME

[75] Inventor: Robert C. Desjarlais, South Hadley, Mass.

[73] Assignee: Scott Paper Company, Philadelphia, Pa.

[22] Filed: Nov. 26, 1974

[21] Appl. No.: 527,409

[52] U.S. Cl. ............................ 96/91 R; 96/49.75; 260/619 R; 260/650 R
[51] Int. Cl.² ........................................ G03C 1/58
[58] Field of Search ...................... 96/91 R, 75.49

[56] References Cited
UNITED STATES PATENTS

| | | | |
|---|---|---|---|
| 2,490,605 | 12/1949 | Von Glahn et al. | 96/91 R |
| 2,516,931 | 8/1950 | Von Glahn et al. | 96/91 R |
| 3,139,341 | 6/1954 | Schlasinger | 96/91 R |
| 3,186,845 | 6/1965 | Sus et al. | 96/91 R |
| 3,294,542 | 12/1966 | Sus et al. | 96/91 R |
| 3,410,688 | 11/1968 | Welch | 96/91 R |
| 3,619,191 | 11/1971 | Desjaulair | 96/91 R |
| 3,650,750 | 3/1972 | Iwata et al. | 96/91 R |

OTHER PUBLICATIONS

Landau, R., "Fascicules 9 & 17," distributed by Andrews Paper Chem. Co., 1962, pp. 18 and 37.
Newman, A., "Brit. J. of Photo.," pp. 281–283, 1963.

Primary Examiner—Charles L. Bowers, Jr.
Attorney, Agent, or Firm—John W. Kane, Jr.; William J. Foley

[57] ABSTRACT

Light-sensitive diazo compositions which comprise a resorcinol substituted in the 2-position with an alkyl group and in the 4-position with an aralkyl group as the yellow azo coupling component, and diazotype materials prepared therefrom.

20 Claims, No Drawings

DIAZO COMPOSITIONS AND DIAZOTYPE MATERIALS PREPARED FROM SAME

BACKGROUND OF THE INVENTION

1. Field of the Invention

The invention relates to diazo compositions which comprise, as the yellow coupling component, a 2-alkyl-4-aralkyl resorcinol, and to diazotype materials prepared therefrom.

2. Description of the Prior Art

It has long been known that diazonium compounds are capable of reacting with compounds such as aromatic amines, phenols, phenol ethers, compounds containing active methylene groups, and the like, to form colored reaction products known as azo dyes. This "coupling" reaction has proven to be most useful in a number of commercial applications, such as in the preparation of textile dyestuffs, and in diazo imaging systems.

Two of the most accepted types of diazo imaging processes employ a diazotype material which comprises a light-sensitive diazonium compound coated on a base or a support material; and, depending on whether or not the diazotype material is designed for use in a one-component or semi-wet development process, or a two-component or "dry" process, the layer or coating containing the light-sensitive diazonium compound may or may not also contain a coupling component for the diazonium compound.

In the case wherein the diazonium compound is present on the base material without a coupling component (i.e., in the case of a one-component or semi-wet development diazotype material), the light-sensitive diazotype material is exposed, and is then developed by applying a developing solution containing a coupling component to the exposed diazotype material. During the exposure step, the light-sensitive diazonium compound is destroyed or altered by the light striking the exposed areas, thereby making the diazonium compound unavailable for coupling with the coupling component in the development step. The subsequent treatment of the exposed diazotype material with the developing solution containing the coupling component results in the formation of an azo dye image in those areas wherein the unaltered diazonium compound is still available for coupling with the coupling component.

In the case wherein the diazonium compound is present on the base material along with a coupling component or components (i.e., in the case of a two-component or dry development diazotype material), the light-sensitive diazotype material is exposed, and is then developed by subjecting the exposed diazotype material to an alkaline atmosphere. As in the case with the one-component diazotype process, the light-sensitive diazonium compound is destroyed or altered by light in the exposed areas during the exposure step, thereby making it unavailable for coupling with the coupling component or components which are present in the diazotype material. When the exposed diazotype material is then subjected to an alkaline atmosphere, such as ammonia, the alkaline conditions permit the coupling reaction to take place between the coupling component and the unaltered diazonium compound to form the colored azo dye image.

Although the color of the azo dye image which is obtained in any given instance depends primarily on the coupling components and the diazonium compounds which are employed, coupling components are often generally described as being couplers of a given color—the color being the color of the dye which is usually obtained when the particular coupler in question couples with a diazonium compound. For example, couplers such as monohydric phenols, catechols, catechol derivatives, resorcinols, resorcinol derivatives, diketones, acetoacetic acid derivatives, acetonitriles, cyanacetylamides and the like, usually result in yellow, orange, sepia, brown, red or maroon azo dyes. Thus, couplers from such classes of materials are conveniently referred to as yellow, orange, sepia, brown, red, or maroon couplers. On the other hand, couplers such as naphthoic acid derivatives, dioxynaphthalene derivatives, pyronones, hydroxypyronones, and the like, usually result in blue or violet azo dyes, and thus are conveniently referred to as blue or violet couplers.

One group of highly useful coupling components are the yellow couplers, since the dyes obtained from these couplers usually have actinic adsorption characteristics which permit their use as the sole coupler is a diazo composition which is employed to prepare diazotype "masters" or intermediates, and since couplers from this group can often be employed as shading components when used in conjunction with another coupler or couplers. As indicated above, compounds containing active methylene groups, compounds such as acetonitriles, derivatives of acetonitriles, and the like, have been employed as yellow couplers in diazo compositions, (cf., for example, U.S. Pats. Nos. 1,989,065; 2,531,004; 2,537,001 and 2,537,106); yet a number of these active-methylene types of couplers have exhibited a tendency, when employed in two-component diazo compositions, to precouple with the diazonium compound which is present in said compositions during storage even in the presence of the stabilizers which are usually employed. This tendency to precouple prior to exposure and development has limited the use of these materials somewhat, since even a slight amount of precoupling can result in the formation of an azo dye in those areas of the diazotype material which are the background or "cleared" areas of the diazotype print. In addition to this tendency to precouple, a number of these prior-art, active-methylene types of couplers also result, upon coupling, in dyes which have an undesirable reddish hue and/or which have a tendency to fade upon subsequent exposure to light.

It should be apparent from the above, that, in addition to obtaining a single-color azo dye image, one should be able to obtain a mixture of azo dyes (and thus a mixture of colors) by including more than one coupling component or more than one diazonium compound in the light-sensitive diazo composition. Thus, by a proper choice of coupling components and/or diazonium compounds, one should be able to obtain a wide variety of colors in the resulting azo dyes, including black. However, the achievement of a uniform color over a wide range of image densities from a diazo composition containing more than one coupling component has proven difficult to obtain in actual practice. In order to obtain a uniform color over a wide range of image densities, it is essential that the coupling activity of the various coupling components with diazonium compound or compounds which are employed be carefully matched, and that the combined absorptions of the azo dyes produced from the various couplers cover the entire visible spectrum. It is also essential that none of the azo dyes produced from the various coupling components be subject to a "color-shift" or change of shade due to a change in pH, else the resulting dye image of the diazotype material may shift from the neutral point.

Thus, although resorcinol sulfides, resorcinol sulfoxides and diresorcinols are several classes of yellow azo coupling components which exhibit excellent resistance to subsequent fading to light, unfortunately these particular classes of yellow coupling components exhibit a severe tendency to color-shift when incorporated into black-line formulations. Similarly, AON's such as 1-hydroxy-2-naphthoic acid piperidide also exhibit a severe tendency to color-shift when incorporated into black-line formulations.

Attempts have also been made to employ alkyl substituted resorcinols (e.g., 2-alkyl resorcinols) and dialkyl substituted resorcinols (e.g., 2,4-dialkyl resorcinols) in blackline formulations. Although the diazotype materials resulting from such formulations exhibit little or no tendency to color-shift, these particular classes of resorcinol coupling components have a relatively slow rate of coupling and are readily oxidized to colored oxidation products.

SUMMARY OF THE INVENTION

Azo coupling components of the general formula:

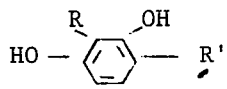

wherein R is a lower alkyl group containing from 1 to about 6 carbon atoms and R' is an aralkyl group wherein the aryl portion of the group either is unsubstituted or is substituted with a halogen atom, a lower alkoxy group containing from 1 to about 6 carbon atoms, or a lower alkyl group containing from 1 to about 6 carbon atoms have been found to be particularly useful as yellow azo coupling components in light-sensitive diazo formulations, exhibiting relatively fast coupling rates and good resistance to oxidation. Diazotype materials prepared from such formulations exhibit excellent storage stability, showing little or no tendency to precouple under normal storage conditions. Blackline materials employing such yellow couplers are light stable (i.e., they show little or no tendency to light-fade) and the resulting dyes exhibit little or no tendency to color shift with changes in pH.

DESCRIPTION OF THE PREFERRED EMBODIMENTS

As hereinbefore indicated, the yellow azo coupling components employed in the light-sensitive diazo formulations of the present invention are resorcinols of the general formula:

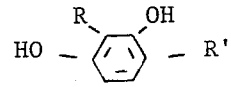

wherein R is a lower alkyl group containing from 1 to about 6 carbon atoms (e.g., methyl, ethyl, propyl, isopropyl, butyl, pentyl, cyclopentyl, hexyl, and the like) and R' is an arakyl group wherein the aryl portion of the group either is unsubstituted or is substituted with a halogen atom (e.g., chloro-, bromo-, and the like), a lower alkoxy group contianing from 1 to about 6 carbon atoms (e.g., methoxy, ethoxy, propoxy, isopropoxy, butoxy, pentoxy, cyclopentoxy, hexoxy, and the like) or a lower alkyl group containing from 1 to about 6 carbon atoms (e.g., methyl, ethyl, propyl, isopropyl, butyl, pentyl, cyclopentyl, hexyl, and the like). Illustrative of such compounds are compounds such as:

2-methyl-4-benzyl resorcinol 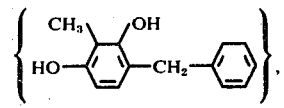, 2-methyl-4-(4'-methyl) benzyl resorcinol 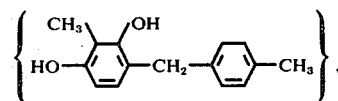, 2-methyl-4-(4'-chloro) benzyl resorcinol 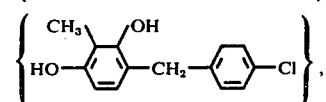, 2-methyl-4-(4'-methoxy) benzyl resorcinol 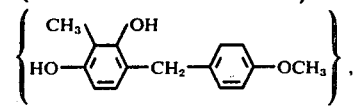, and the like. Such compounds can be prepared by reacting a 2-alkyl resorcinol such as 2-methyl resorcinol with an aralkyl halide such as benzyl chloride, p-methoxybenzyl chloride, and the like.

The light-sensitive diazonium compounds which can be employed in preparing the light-sensitive diazo compositions of the present invention are any of the numerous light-sensitive diazonium compounds which are available in the prior art, and the particular light-sensitive diazonium compound which is employed is not critical in the practice of this invention. Illustrative of such compounds are the stabilized salts or double salt complexes of diazonium derivatives of a p-phenylenediamine, for example, stabilized salts of diazonium derivatives of such compounds as N-methyl-p-phenylenediamine, N-ethyl-p-phenylenediamine, N-hydroxyethyl-p-phenylene-diamine, N,N-dimethyl-p-phenylenediamine, N,N-diethyl-p-phenylenediamine, N,N-dipropyl-p-phenylenediamine, N-methyl-N-(β-hydroxyethyl)-p-phenylenediamine, N-ethyl-N-(β-hydroxyethyl)-p-phenylenediamine, N-(β-hydroxyethyl)-p-phenylenediamine, N-butyl-N-(β-hydroxyethyl)-p-phenylenediamine, N,N-di(β-hydroxyethyl)-p-phenylenediamine, N-benzyl-N-ethyl-p-phenylenediamine, N-ethyl-2-methyl-4-aminoaniline, N,N-dimethyl- 2-methyl-4-aminoaniline, N,N-dimethyl-3-methyl-4-aminoaniline, N,N-diethyl-3-methyl-4-aminoaniline, N-ethyl-N-(β-hydroxyethyl)-3-methyl-4-aminoaniline, N-cyclohexyl-2-methoxy-4-aminoaniline, N,N-di(β-hydroxyethyl)-3-methyl-4-aminoaniline, 2,5-diethoxy-4-morpholinoaniline, 2,5-dimethoxy-4-morpholinoaniline, 2,5-dibutoxy-4-morpholinoaniline, 2,5-diisopropoxy-4-morpholinoaniline, 2,5-diethoxy-4-piperidinoaniline, 2,5-dimethoxy-4-piperidinoaniline, 2,5-diisopropoxy-4-(N'-benzoyl)piperazinoaniline, N-benzyl-2,5-diethoxy-4-aminoaniline, 2,6-dimethyl-4-morpholinoaniline, 2,6-diethyl-4-morpholinoaniline, 2,6-dimethyl-4-piperidinoaniline, and the like.

The nature of the salt used to stabilize or complex the diazonium derivative is not critical, and can be, for example, a zinc chloride double salt, a cadmium chloride double salt, a tin chloride double salt, a borofluoride salt, a sulfate salt, a hexafluorophosphate salt, and the like.

It should be understood that mixtures of light-sensitive diazonium compounds can be employed in the practice of the present invention without departing from the scope thereof, and that other couplers can be employed in conjunction with the yellow couplers hereinbefore described in preparing diazo compositions in accordance with the present invention without departing from the scope thereof. In this regard, of particular interest are black-line diazo compositions comprising one or more couplers from the particular class of yellow azo coupling components set forth above in full detail, along with one or more light-sensitive diazonium compounds and one or more BON blue azo coupling components such as 2-hydroxy-3-naphthoic acid, 2'-methoxy-aniline; 2-hydroxy-3-naphthoic acid,2'5'-dimethylanide; and the like. Such black-line formulations provide black-line diazotype materials which are light-stable (i.e. are fade resistant), are storage-stable (i.e. are resistant to precoupling), are resistant to color-shift with changes in pH.

The light-sensitive diazo compositions of this invention can also comprise any of the additional components which are often employed in such compositions, such as stabilizers, preservatives, anti-oxidants, extenders, inhibitors, color intensifiers, and the like.

The various components of the light-sensitive diazo compositions of this invention are usually dissolved in an organic solvent system, and the resulting solution is then coated, using conventional coating techniques, onto a suitable base support. The base supports which can be employed are any of those commonly used as support materials in the photographic and copying arts, such as paper, cloth, films and the like. Illustrative of the films which can be employed are films such as cellulose ether films, cellulose ester films (e.g., cellulose acetate and cellulose acetate butyrate) polyester films (e.g., polyethylene terephthalate), and the like. Upon drying, the base support which has been coated with a light-sensitive diazo composition of this invention results in a light-sensitive diazotype material which can then be imaged and developed in the manner which is conventional and well-known in the diazotype art. Such diazotype materials find use in the fields of engineering drawing reproduction, microfilm duplication, visual communications and the graphic arts.

The following preparations are provided to illustrate more specifically methods of preparing several of the yellow couplers which are an essential component of the diazo compositions of this invention. In these preparations, as well as in the examples illustrating the invention which follow, all parts and percentages are parts and percentages by weight and not by volume, unless specifically stated otherwise in the particular preparation or example.

Preparation of 2-methyl-4-benzyl resorcinol, 2-methyl-4-(4'-chloro) benzyl resorcinol and 2-methyl-4-(4'-methyl) benzyl resorcinol.

31 grams (0.25 mole) of 2-methylresorcinol were dissolved in 75 milliliters of hot toluene, and then 0.34 grams of dry zinc chloride was added. This mixture was then brought to reflux and 31.6 grams (0.25 mole) of benzyl chloride were added, dropwise, over a six-hour period. Upon completion of this addition, reflux of the resulting reddish solution was continued for another half hour, after which period of time toluene was distilled off under reduced pressure. The liquid residue remaining after the removal of the toluene was poured into cold water and stirred for one hour. This mixture was then filtered and dried to yield 40.2 grams of a light-brown, waxy solid. Analysis of this solid via gas chromatography indicated that it was comprised of 70% of 2-methyl-4-benzyl resorcinol and 30% of 2-methyl resorcinol, monobenzyl ether. This latter component was extracted with hot hexane and the remaining 2-methyl-4-benzyl resorcinol was recrystallized from a mixture of toluene and hexane to yield 21.2 grams of the purified 2-methyl-4-benzyl resorcinol product which melted from 95 to 97.5°C. 2-Methyl-4-(4'-chloro) benzyl resorcinol and 2-methyl-4-(4'-methyl) benzyl resorcinol were prepared in a similar manner, using, respectively, 4-chlorobenzyl chloride and 4-methyl benzyl chloride in place of the benzyl chloride. The 2-methyl-4-(4'-chloro) benzyl resorcinol which was obtained had a melting point of from 86° to 90.5°C., and the 2-methyl-4-(4'-methyl) benzyl resorcinol which was obtained had a melting point of from 116° to 122°C.

Preparation of 2-methyl-4-(4'-methoxy) benzyl resorcinol 4.95 Grams of 2-methyl resorcinol (0.032 mole) and 5 grams of 4-methoxybenzyl chloride (0.032 mole) were refluxed in 20 milliliters of xylene for 18 hours. Upon cooling, a solid white mass formed. The solid obtained was filtered, washed first with a small amount of xylene, and then with a mixture of hexane and heptane. The solid was then recrystallized from an aqueous solution of 75% formic acid to yield 2.6 grams of 2-methyl-4-(4'-methoxy) benzyl resorcinol having a melting point of from 80° to 89°C. Thin layer chromatography disclosed the presence of a small amount of a non-coupling component in the product which was obtained.

The following examples are intended to further illustrate the invention disclosed and claimed herein, but they are not intended to limit the scope thereof in any way. The first time that a particular component is mentioned in any of the following examples, an attempt will be made to describe its intended function in parentheses immediately following the enumeration of the component itself. When the same component is mentioned thereafter in any of the following examples, a recitation of its intended function will be omitted unless the intended function is different from that given upon the first enumeration of such component. Where it is believed that the structural formula of any given component might be of some assistance, such formula will also be provided upon first enumeration of the component in question.

EXAMPLE 1

A light-sensitive coating formulation was prepared containing the following components:

| Component | Amount |
|---|---|
| Methanol (Solvent) | 5.0 Grams |
| Acetone (Solvent) | 95.0 Grams |
| Hexafluorophosphoric acid (Acidic Stabilizer) | 0.3 Grams |
| 2-Hydroxy-3-naphthoic acid, 2',5'-dimethyl-anilide (Azo Coupling Component) | 0.38 Grams |
| 2-Hydroxy-3-naphthoic acid, 2'-methoxy-anilide (Azo Coupling Component) | 0.66 Grams |
| 2-Methyl-4-benzyl resorcinol (Azo Coupling Component) | 1.36 Grams |
| 4-(N-methyl) aminobenzene diazonium hexafluorophosphate (Light-sensitive Diazonium Compound) | 0.74 Grams |
| 2,5-Diisopropoxy-4-(N'-benzoyl) piperazinobenzene diazonium hexafluorophosphate (Light-sensitive Diazonium Compound) | 1.45 Grams |
| Tributyl citrate (Development Accelerator) | 1.65 Grams |

This formulation was then bead-coated onto a polyester film which had previously been pretreated with a suitable bonding layer and subbed with a cellulose acetate propionate layer. After drying, the resulting diazotype material was exposed to a Gallium doped mercury vapor arc light source using a Kodak photograhic step wedge as a master. The exposed diazotype material was then developed by subjecting the material to the ammonia vapors present in an "Ozamatic" diazo processor. An intense, low-contrast, neutral black image was obtained which, after airing to free the print of any residual ammonia vapors, was essentially unchanged from that obtained initially. Substitution of 2,2',4,4'-tetrahydroxy-3,3'-dimethyldiphenyl sulfide; 2,2',4,4'-tetrahydroxy-3,3'-dimethyldiphenyl sulfoxide or 1-hydroxy-2-naphthoic acid piperidide for the 2-methyl-4-benzyl resorcinol in the above formulation results in diazotype materials which, upon development, yield prints which are initially plum colored, although these print eventually color-shift to a neutral black upon standing.

EXAMPLES 2 to 5

Light-sensitive coating formulations were prepared containing the following components:

| Component | Ex. 2 | | Ex. 3 | | Ex. 4 | | Ex. HO | |
|---|---|---|---|---|---|---|---|---|
| | | Grams | | Grams | | Grams | | Grams |
| Methanol | 52 | | 52 | | 52 | | 52 | |
| Acetone | 30 | " | 30 | " | 30 | " | 30 | " |
| Methyl Ethyl Ketone (Solvent) | 10 | " | 10 | " | 10 | " | 10 | " |
| 2-Hydroxy-3 naphthoic acid, 2',5'-dimethyl-anilide | 0.92 | " | 0.92 | " | 0.92 | " | 0.92 | " |
| Hexafluorophosphoric acid | 0.40 | " | 0.40 | " | 0.40 | " | 0.40 | " |
| 2,5-diisopropoxy-4-(N'-benzoyl) piperazine-benzene diazonium hexafluorophosphate | 3.05 | " | 3.05 | " | 3.05 | " | 3.05 | " |
| Tributyl citrate | 3.0 | " | 3.0 | " | 3.0 | " | 3.0 | " |
| 2-Methyl-4 benzyl resorcinol | 1.97 | " | | | | | | |
| 2-Methyl-4-(4' methyl) benzyl resorcinol (Azo Coupling Component) | | | 2.10 | " | | | | |
| 2-Methyl-4-(4' chloro) benzyl resorcinol (Azo Coupling Component) | | | | | 2.29 | " | | |
| 2-Methyl-4-(4'-methoxy) benzyl resorcinol | | | | | | | | |

| Component (Azo Coupling Component) | Ex. 2 | Ex. 3 | Ex. 4 | Ex. HO |
|---|---|---|---|---|
| | | | | 2.24 " |

Each of these formulations was separately bead-coated onto a polyester film which had previously been pretreated with a suitable bonding layer and subbed with a 20 second cellulose acetate propionate layer. After drying for 10 minutes at 70°C., the resulting diazotype materials were exposed to light using a Kodak photographic step wedge as a master. The exposed diazotype materials were then developed in hot ammonia vapors. After airing for one hour and then comparing the resulting diazotype materials with a set of freshly developed prints, no discernable change in image color could be observed. In addition, the intense neutral black image was evident over a wide range of densities on the photographic step wedge obtained with each of the diazotype materials. Substitution of 2,2',4-,4'-tetrahydroxy-3,3'-dimethyldiphenyl sulfide; 2,2',4-,4'-tetrahydroxy-3,3'-dimethyldiphenyl sulfoxide;-diresorcinol sulfide; diresorcinol sulfoxide or 1-hydroxy-2-naphthoic acid piperidide for the 2-alkyl-4-aralkyl resorcinols in the above formulations results in diazotype materials which, upon development, yield prints which are initially plum colored, although these print eventually color-shift to a neutral black upon standing. Since the 2-methyl-4 aralkyl-substituted resorcinols employed in these examples (Examples 2 to 5) exhibited essentially the same coupling rates and they all produced a neutral black image over a wide range of image densities, they obviously can be interchanged for one another in these or similar formulations with little or no deleterious effects or noticeable differences.

What is claimed is:

1. A light-sensitive diazo composition which comprises at least one light-sensitive diazonium compound, an acidic stabilizer, and an azo coupling component of the general formula:

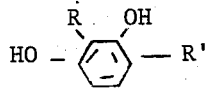

wherein R is a lower alkyl group containing from 1 to about 6 carbon atoms and R' is an aralkyl group wherein the aryl portion of the group either is unsubstituted or is substituted with a halogen atom, a lower alkoxy group containing from 1 to about 6 carbon atoms, or a lower alkyl group containing from 1 to about 6 carbon atoms.

2. A light-sensitive diazo composition as claimed in claim 1 wherein the azo coupling component is a compound having the structural formula:

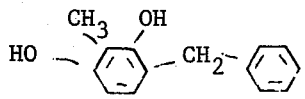

3. A light-sensitive diazo composition as claimed in claim 1 wherein the azo coupling component is a compound having the structural formula:

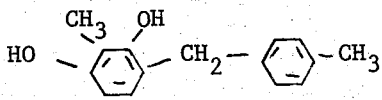

4. A light-sensitive diazo composition as claimed in claim 1 wherein the azo coupling component is a compound having the structural formula:

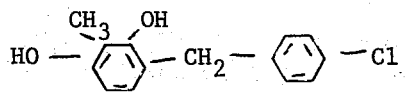

5. A light-sensitive diazo composition as claimed in claim 1 wherein the azo coupling component is a compound having the structural formula:

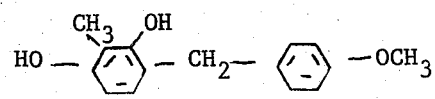

6. A light-sensitive diazo composition as claimed in claim 2 wherein the acidic stabilizer is hexafluorophosphoric acid, the light-sensitive diazonium compound is 2,5-diisopropoxy -4-(N'-benzoyl) piperazinobenzene diazonium hexafluorophosphate, and wherein 2-hydroxy-3-naphthoic acid, 2',5'-dimethylanilide is employed as an additional azo coupling component.

7. A light-sensitive diazo composition as claimed in claim 6 which comprises 4-(N-methyl) aminobenzene diazonium hexafluorophosphate as an additional light-sensitive diazonium compound and 2-hydroxy-3-naphthoic acid, 2'-methoxyanilide as an additional azo coupling component.

8. A light-sensitive diazo composition as claimed in claim 3 wherein the acidic stabilizer is hexafluorophosphoric acid, the light-sensitive diazonium compound is 2,5-diisopropoxy -4-(N'-benzoyl) piperazinobenzene diazonium hexafluorophosphate, and wherein 2-hydroxy-3-naphthoic acid, 2',5'-dimethylanilide is employed as an additional azo coupling component.

9. A light-sensitive diazo composition as claimed in claim 4 wherein the acidic stabilizer is hexafluorophosphoric acid, the light-sensitive diazonium compound is 2,5-diisopropoxy-4-(N'-benzoyl) piperazinobenzene diazonium hexafluorophosphate, and wherein 2-hydroxy-3-naphthoic acid, 2',5'-dimethylanilide is employed as an additional azo coupling component.

10. A light-sensitive diazo composition as claimed in claim 5 wherein the acidic stabilizer is hexafluorophosphoric acid, the light-sensitive diazonium compound is 2,5-diisopropoxy-4-(N'-benzoyl) piperazinobenzene diazonium hexafluorophosphate, and wherein 2-hydroxy-3-naphthoic acid, 2',5'-dimethylanilide is employed as an additional azo coupling component.

11. A light-sensitive diazotype material which comprises a base support having a coating thereon which is a light-sensitive diazo composition as claimed in claim 1.

12. A light-sensitive diazotype material which comprises a base support having a coating thereon which is a light-sensitive diazo composition as claimed in claim 2.

13. A light-sensitive diazotype material which comprises a base support having a coating thereon which is a light-sensitive diazo composition as claimed in claim 3.

14. A light-sensitive diazotype material which comprises a base support having a coating thereon which is a light-sensitive diazo composition as claimed in claim 4.

15. A light-sensitive diazotype material which comprises a base support having a coating thereon which is a light-sensitive diazo composition as claimed in claim 5.

16. A light-sensitive diazotype material which comprises a base support having a coating thereon which is a light-sensitive diazo composition as claimed in claim 6.

17. A light-sensitive diazotype material which comprises a base support having a coating thereon which is a light-sensitive diazo composition as claimed in claim 7.

18. A light-sensitive diazotype material which comprises a base support having a coating thereon which is a light-sensitive diazo composition as claimed in claim 8.

19. A light-sensitive diazotype material which comprises a base support having a coating thereon which is a light-sensitive diazo composition as claimed in claim 9.

20. A light-sensitive diazotype material which comprises a base support having a coating thereon which is a light-sensitive diazo composition as claimed in claim 10.

* * * * *